United States Patent
Abeliuk et al.

(10) Patent No.: US 12,315,599 B2
(45) Date of Patent: May 27, 2025

(54) METHOD, APPARATUS, AND COMPUTER-READABLE MEDIUM FOR OPTIMAL POOLING OF NUCLEIC ACID SAMPLES FOR NEXT GENERATION SEQUENCING

(71) Applicant: TeselaGen Biotechnology Inc., San Francisco, CA (US)

(72) Inventors: Eduardo Abeliuk, Oakland, CA (US); Andrés Igor Pérez Manríquez, Santiago (CL); Juan Andrés Ramírez Neilson, Santiago (CL); Diego Francisco Valenzuela Iturra, Santiago (CL)

(73) Assignee: TESELAGEN BIOTECHNOLOGY INC., San Francisco, CA (US)

( * ) Notice: Subject to any disclaimer, the term of this patent is extended or adjusted under 35 U.S.C. 154(b) by 570 days.

(21) Appl. No.: 17/219,474

(22) Filed: Mar. 31, 2021

(65) Prior Publication Data

US 2021/0304844 A1    Sep. 30, 2021

Related U.S. Application Data

(60) Provisional application No. 63/002,864, filed on Mar. 31, 2020.

(51) Int. Cl.
*G16B 30/00* (2019.01)
*C12Q 1/6869* (2018.01)

(52) U.S. Cl.
CPC ........... *G16B 30/00* (2019.02); *C12Q 1/6869* (2013.01)

(58) Field of Classification Search
CPC ..................................................... G16B 30/00
See application file for complete search history.

(56) References Cited

U.S. PATENT DOCUMENTS

2022/0005547 A1* 1/2022 Ye .................... G16B 25/10

OTHER PUBLICATIONS

McComish et al., Index-Free De Novo Assembly and Deconvolution of Mixed Mitochondrial Genomes, 2010, Genome Biol. Evol., 2, p. 410-424 (Year: 2010).*

* cited by examiner

*Primary Examiner* — Kaitlyn L Minchella
(74) *Attorney, Agent, or Firm* — Amardeep S. Grewal; Reed Smith LLP

(57) ABSTRACT

A method, apparatus, and computer-readable medium for optimal pooling of nucleic acid samples for next generation sequencing, including receiving sample records corresponding to samples, each sample record comprising a sample identifier and a nucleic acid reference sequence of the sample, determining unique nucleic acid reference sequences in the sample records, computing, a nucleic acid overlaps between the unique nucleic acid reference sequences, and determining an optimal grouping of the plurality of samples into a plurality of sample pools based at least in part on the nucleic acid reference sequence of each sample record, the nucleic acid overlaps between the unique nucleic acid reference sequences, and one or more constraints, the one or more constraints including a maximum overlap constraint.

24 Claims, 12 Drawing Sheets

$$\begin{bmatrix} x_{11} & x_{12} & x_{13} & x_{14} & x_{15} \\ x_{21} & x_{22} & x_{23} & x_{24} & x_{25} \\ x_{31} & x_{32} & x_{33} & x_{34} & x_{35} \\ x_{41} & x_{42} & x_{43} & x_{44} & x_{45} \\ x_{51} & x_{52} & x_{53} & x_{54} & x_{55} \\ x_{61} & x_{62} & x_{63} & x_{64} & x_{65} \\ x_{71} & x_{72} & x_{73} & x_{74} & x_{75} \\ x_{81} & x_{82} & x_{83} & x_{84} & x_{85} \\ x_{91} & x_{92} & x_{93} & x_{94} & x_{95} \end{bmatrix}$$

Solution Matrix (unsolved)

Fig. 8

Solution Matrix (resolved)

$$\begin{matrix} & 1 & 2 & 3 & 4 & 5 \\ 1 & 1 & 1 & 1 & 0 & 0 \\ 2 & 1 & 1 & 0 & 1 & 0 \\ 3 & 0 & 1 & 0 & 0 & 0 \\ 4 & 0 & 0 & 0 & 0 & 1 \\ 5 & 0 & 0 & 0 & 0 & 1 \\ 6 & 0 & 0 & 0 & 0 & 0 \\ 7 & 0 & 0 & 0 & 0 & 0 \\ 8 & 0 & 0 & 0 & 0 & 0 \\ 9 & 0 & 0 & 0 & 0 & 0 \end{matrix}$$

Fig. 9

Solution Matrix (resolved)

$$\begin{matrix} & 1 & 2 & 3 & 4 & 5 \\ 1 & 1 & 1 & 1 & 0 & 0 \\ 2 & 1 & 1 & 0 & 1 & 0 \\ 3 & 0 & 1 & 0 & 0 & 0 \\ 4 & 0 & 0 & 0 & 0 & 1 \\ 5 & 0 & 0 & 0 & 0 & 1 \\ 6 & 0 & 0 & 0 & 0 & 0 \\ 7 & 0 & 0 & 0 & 0 & 0 \\ 8 & 0 & 0 & 0 & 0 & 0 \\ 9 & 0 & 0 & 0 & 0 & 0 \end{matrix}$$

1000

Solution Matrix (balanced)

$$\begin{matrix} & 1 & 2 & 3 & 4 & 5 \\ 1 & 0 & 1 & 1 & 0 & 0 \\ 2 & 1 & 0 & 0 & 1 & 0 \\ 3 & 1 & 1 & 0 & 0 & 0 \\ 4 & 0 & 1 & 0 & 0 & 1 \\ 5 & 0 & 0 & 0 & 0 & 1 \\ 6 & 0 & 0 & 0 & 0 & 0 \\ 7 & 0 & 0 & 0 & 0 & 0 \\ 8 & 0 & 0 & 0 & 0 & 0 \\ 9 & 0 & 0 & 0 & 0 & 0 \end{matrix}$$

| Task | a) Without Sample Multiplexing | b) Manual Sample Multiplexing | c) Disclosed Optimized Sample Multiplexing |
|---|---|---|---|
| | Solution | 200 sequencing elements | 100 sequencing elements | 60 sequencing elements |
| | Machine time | 0 hours | ≈ 5 minutes | 156 seconds |
| A | M/H time | 0 hours | 1 day | 2 minutes |
| | Sequencing cost | 1,180 USD | 590 USD | 354 USD |
| | M/H cost | 0 USD | 205.2 USD | 1 USD |
| | Total time | 0 hours | 1 day | 4 minutes |
| | Total cost | 1,180 USD | 795.2 USD | 355 USD |

Fig. 12

METHOD, APPARATUS, AND COMPUTER-READABLE MEDIUM FOR OPTIMAL POOLING OF NUCLEIC ACID SAMPLES FOR NEXT GENERATION SEQUENCING

RELATED APPLICATION DATA

This application claims priority to U.S. Provisional Application No. 63/002,864, filed Mar. 31, 2020, and titled "SYSTEM AND METHOD FOR OPTIMIZING SAMPLE MULTIPLEXING IN NEXT GENERATION SEQUENCING (NGS)," the disclosure of which is hereby incorporated by reference in its entirety.

BACKGROUND

Next generation sequencing (NGS) refers to the usage of the different state-of-the-art deoxyribonucleic acid (DNA) sequencing technologies. These allow sequencing DNA and ribonucleic acid (RNA) much more rapidly and cheaply than previous techniques. All NGS platforms are today able to perform sequencing of millions of small fragments of DNA in parallel. Bioinformatics and data analyses are then used to piece together these fragments by mapping the individual fragment reads to a reference genome. Each fragment of DNA or RNA is read multiple times in order to increase the machine's reading accuracy or coverage. NGS can be used to sequence either entire genomes or rather specific areas of interest within a genome.

All NGS procedures require a "sample preparation" process before the actual sequencing. This means generating, from the original sequence, what is known as a "sample library", which is the actual input to the NGS sequencing machines. The sample library is the result of a two-step process: "fragmentation" and "amplification." Fragmentation is needed because all NGS methods have poor reading accuracy on large DNA sequences. In broad terms, fragmentation is done by randomly cutting the original sequence into smaller pieces and attaching tags or adapters to each end of a fragment. These adapters are then used in the "amplification" step preferably performed by PCR (Polymerase Chain Reaction). Quantitative and qualitative control is recommended after these two steps to check if the fragmentation and amplification processes resulted in an appropriate sample library for sequencing.

Once the sample library is successfully generated, it is passed to the NGS machine to execute the sequencing step. This machine will read the DNA fragments and generate an electronic file containing the nucleotide base pair "calls" read from the sample library. A final bioinformatic data analysis step is done to map these fragment reads to the original sequence.

Sample multiplexing is a technique which allows for multiple sample libraries to be pooled together and be sequenced by the NGS machine simultaneously. This reduces time and costs because instead of sequencing each sample library at a time, multiplexing allows the process to be parallelized. Two ways of performing multiplexing include barcode sequencing and mixing DNA sample libraries together (without barcodes).

Barcode sequencing is done in the fragmentation step by adding a "barcode" sequence to the adapters attached to each fragment. A barcode sequence is a small and unique sequence of a few nucleotide base pairs. Each sequence being multiplexed will use a unique barcode identifying its fragments, which then allows the correct identification of each fragment in order to map them back to their corresponding sample library.

As an alternative to barcode sequencing, DNA sample libraries can be mixed together without barcodes. When performing this mixing, the DNA of each sample library has to be sufficiently different, otherwise the identification of each fragment will not be possible, and mapping them back to their original sample libraries becomes unfeasible.

Unfortunately, both of these approaches have drawbacks. Barcode sequencing requires designing and synthesizing individual DNA barcodes, performing additional DNA ligation steps and then performing a computational demultiplexing step to map the sequenced fragment to the original sample library, which comes with significant time and economic costs. Additionally, automating the mixing approach is non-trivial for large numbers of sample libraries due to the numerous ways of mixing different DNA samples together, and the number of pooling constraints.

Accordingly, improvements are needed in technology for optimizing multiplexing for next generation sequencing.

BRIEF DESCRIPTION OF THE DRAWINGS

FIG. 8 illustrates an example of a solution matrix according to an exemplary embodiment.

FIG. 9 illustrates an example of a resolved solution matrix according to an exemplary embodiment FIG. 10 illustrates an example of pool balancing according to an exemplary embodiment.

FIG. 12 illustrates a table with experimental results showing the specific technical advantages and improvements of the present system relative to previous systems.

DETAILED DESCRIPTION

Figure 1:
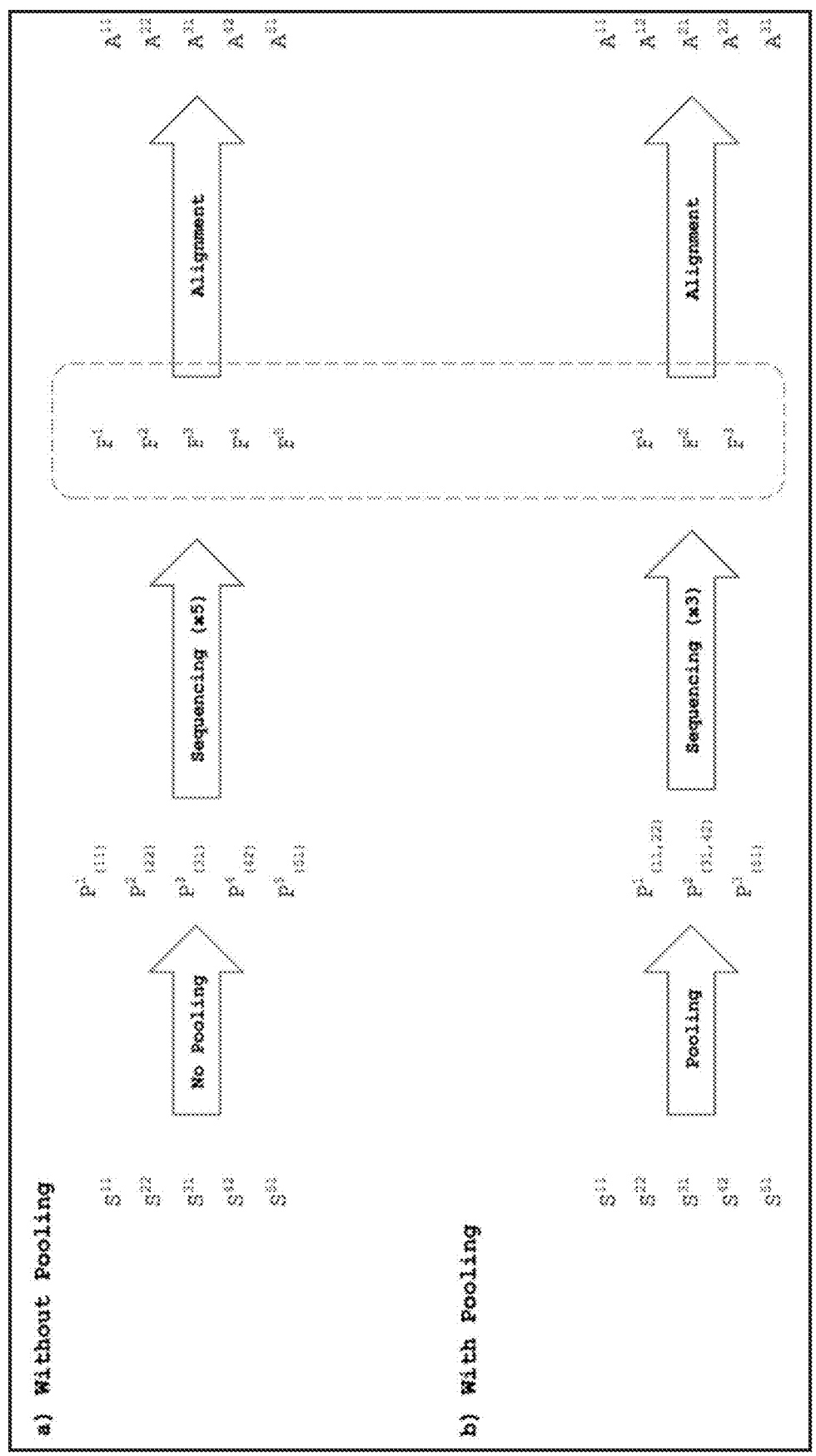
FIG. 1 illustrates the advantages of pooling samples when performing DNA or RNA sequencing.

While methods, apparatuses, and computer-readable media are described herein by way of examples and embodiments, those skilled in the art recognize that methods, apparatuses, and computer-readable media for optimal pooling of DNA or RNA samples are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "can" is used in a permissive sense (i.e., meaning having the potential to) rather than the mandatory sense (i.e., meaning must). Similarly, the words "include," "including," and "includes" mean including, but not limited to.

As discussed above, the mixing approach to multiplexing has the drawback of being computationally inefficient. Specifically, an optimal solution to determining which DNA samples to pool can be attained with a brute force approach, in which a scientist runs an alignment algorithm on all the DNA samples, and then uses a computer to find all the possible sets of combinations in order to finally choose the best one. This approach is very inefficient, and without considering the pooling constraints, has a computational complexity (i.e., Big O) on the order of:

$$O\left(\frac{n!}{k! \times (n-k)!}\right)$$

Where 'n' is the number of sample libraries, and 'k' the number of sample libraries per pool or group. This computational complexity makes the use of a brute force approach infeasible for many applications, as well as being time consuming and an inefficient use of limited computing power.

Applicant has discovered a novel system and method for optimizing the sample multiplexing process used in Next Generation Sequencing (NSG). Applicant's specialized solution computes an algorithm aided with a linear optimization solver and allows for optimal pooling of nucleic acid (DNA or RNA) samples for next generation sequencing Applicant's solution runs an algorithm implemented in a computer program that analyzes the DNA similarities of the set of sample libraries to be submitted for sequencing in a computationally efficient manner and returns a solution indicating which sample libraries are able to be mixed together (or pooled together) without losing the ability to map the DNA fragments back to their corresponding sample libraries. Importantly, the algorithm can handle biologically relevant constraints (such as being able to handle samples containing either linear DNA or circular DNA).

Applicant notes that although the present application sometimes refers to DNA and DNA sequencing, the techniques disclosed herein can be utilized for any type of nucleic acid. In particular, the techniques disclosed herein can equally be applied to ribonucleic acid (RNA) sequencing without departing from the scope of the description or the disclosed steps.

The following terms are used in this application. A brief description of each term is provided below, but this description is not intended to limit the meaning or scope of the relevant terms.

Samples: these represent physical elements with an associated reference DNA or RNA sequence. These elements are the ones that are going to be sequenced by the NGS machine. By this definition, many samples may share the same DNA or RNA reference sequence.

Reference sequences: these are the DNA or RNA sequence of nucleotide characters (A, C, G and T) representing the DNA or RNA of the above mentioned samples. At the bioinformatic data analysis stage, the NGS machine outputs an electronic file in FASTQ format. This file contains a list of nucleotide sequences, with their corresponding probabilities of being correctly read, that were identified by the machine when reading the DNA or RNA fragments. These readings are then mapped to the original reference sequences. Many times a user or lab will attempt to synthesize, replicate, or otherwise create a particular DNA/RNA sequence in a sample. The reference sequence can indicate the anticipated structure of the that DNA/RNA sequence, which is subject to validation and verification via sequencing of the sample by the NGS machine.

Sample libraries: these correspond to the product of the "two-step sample preparation" process performed for each sample. Each sample library contains many smaller DNA OR RNA fragments coming from the fragmentation and amplification of the original sample DNA or RNA sequence.

Sample Pools: these are representations of the physical elements containing a mix or pool of different sample libraries.

Sequencing Elements: these correspond to the actual physical elements that are going to be used as input to an NGS machine. These elements are put into any laboratory container that the NGS machine requires. These containers can have one or many sample libraries inside.

In addition to the above terms, the following symbols are used in this document. Note that superscripts 'k', 'j' and 'm' represent integer numbers.

$R^k$: a DNA/RNA reference sequence 'k'.

$S^{jk}$: a unique sample 'j' with reference sequence $R^k$.

$P^m$ ( . . . ): a unique pool 'm', containing a specific number of samples. The parenthesis '( . . . )' will include the samples of the pool represented only by their 'jk' superscript indexes (i.e.: "$P^1$ (11, 12, 21)").

$F^m$: a unique output file 'm', coming from sequencing the $m^{th}$ pool by an NGS machine.

$A^{mk}$: Represents an alignment/mapping between the fragment reads of the $m^{th}$ output file and the reference sequence $R^k$.

An objective of the disclosed system and method is to improve the DNA sequencing process to increase efficiency and reduce time required to produce a solution by optimizing sample multiplexing (mixing DNA or RNA sample libraries together without barcoding). This is accomplished by pooling together, as much samples as possible, which will parallelize the process of sequencing a set of samples.

FIG. 1 illustrates the advantages of pooling samples when performing DNA or RNA sequencing. The figure illustrates an example of the sequencing and alignment steps for five samples, both with and without pooling. The five samples have reference sequences R1 and R2. Samples 1, 3 and 5 have R1 as their reference sequence, while samples 2 and 4 have reference sequence R2. When no pooling is performed, these 5 samples are sequenced alone (not pooled), represented by the five one-element pools. When pooling is performed, these 5 samples go through the pooling phase reducing the sequencing elements from five to three (two two-element pools and a single-element pool). After sequencing, the electronic output files corresponding to each sequenced pool are used to perform the fragment mapping with next generation sequencing alignment procedures with the corresponding R1 and R2 as the reference sequences. In both cases, 5 alignments will be generated, corresponding to each original sample, but the pooling step results in a 40% reduction in sequencing runs.

The disclosed method, apparatus, and computer-readable medium efficiently determines which sample libraries can be pooled together into the same sequencing element. In order to group different sample libraries into the same sequencing element they must comply with important constraints based on the DNA/RNA similarities of their respective reference sequences. The main constraint is that only those groups of sample libraries whose DNA/RNA overlap lengths are all lower than a certain threshold (lower than the DNA/RNA fragment's length) can be put in the same sequencing element (i.e. pool). This latter constraint is crucial because if the DNAs or RNAs of the mixed sample libraries are very similar, it will become infeasible to map the DNA or RNA fragments of a sequencing element back to their corresponding sample library.

Figure 2:
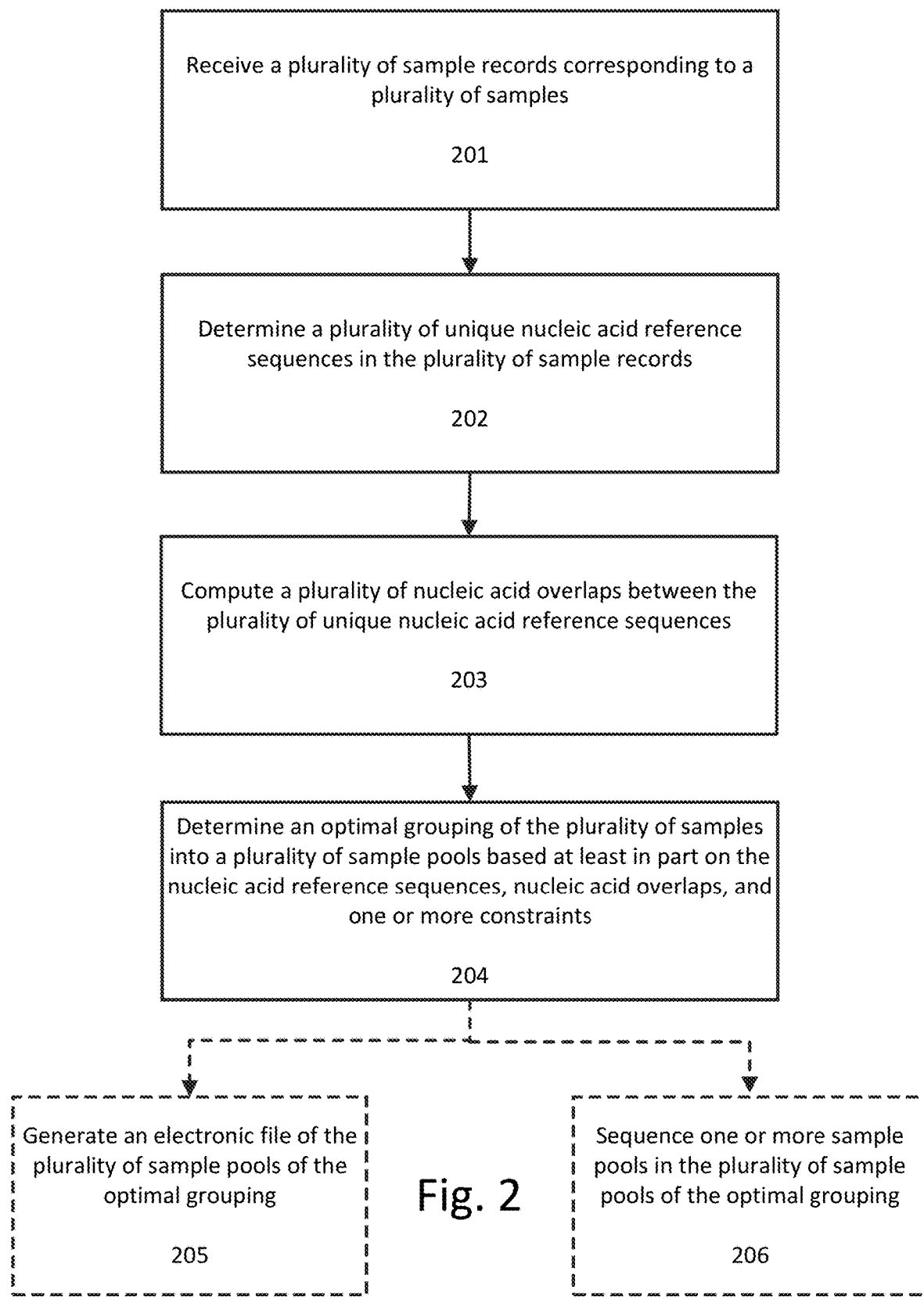
FIG. 2 illustrates a flowchart for optimal pooling of nucleic acid samples for next generation sequencing according to an exemplary embodiment.

FIG. 2 illustrates a flowchart for optimal pooling of nucleic acid samples for next generation sequencing according to an exemplary embodiment. As discussed previously, the nucleid acid samples can be DNA samples or RNA samples.

At step 201 a plurality of sample records corresponding to a plurality of samples are received, each sample record comprising a sample identifier and a nucleic acid reference sequence of the sample. The sample records can be read from a file, retrieved from a network location, input by a user, or otherwise entered into the system. The sample records can be parsed and stored in a list or other data structure.

The sample records are an electronic representation of samples and can be received in any suitable format. Each sample record can include the following parameters/variables:

Each sample record includes a nucleic acid (DNA/RNA) reference sequence. As discussed above, these are the DNA or RNA sequence of nucleotide characters (A, C, G and T) representing the DNA or RNA of the sample.

Optionally, one or more annotations can also be part of the sample record. The annotations can be represented, for example, as string arrays. The annotations can include information from publically available nucleotide sequence databases, such as GenBank. This can include each annotation's start and end base pair loci (e.g., as integers), each annotation's name (e.g., as a string), each annotation's biological type (e.g., as a string), each annotation's biological notes (e.g., as a string).

Each sample record also includes a nucleic acid type variable (also referred to as a "Circular DNA" variable). This variable can be a Boolean flag which indicates whether the sample and nucleic acid reference sequence comprise circular DNA or non-circular (linear) DNA. This information is utilized at the overlap assessment stage, as discussed further below.

Optionally, each sample record can also include an "Ignore" variable, which can be a Boolean variable used to exempt certain samples from the analysis, multiplexing, or pooling. This variable can be used if a specific sample from the sample set wants to be ignored by the algorithm. If the Ignore variable is set to true, it won't be considered in the optimization and it will be left alone in a single-element pool.

Additional inputs to the system include the maximum tuple size (i.e., the maximum number of samples in a pool), exclude annotations, and exclusive annotations. Exclude annotations are a list of annotations to exclude from the overlap determination step (discussed below). This is used when the user wants to exclude certain DNA regions of the reference sequence from the overlap computation step. Exclusive Annotations are a list of annotations from which to compute the overlaps. This is used when the user wants to compute overlaps only on certain regions of the reference sequence for the overlap computation step. The exclude annotations and exclusive annotations can be part of each sample record or can be input globally and applied to each of the sample records.

At step 202 a plurality of unique nucleic acid reference sequences in the plurality of sample records are determined. This step can include making a list of all sample records and then making a list of all non-duplicated reference sequences of the sample records. For example, this step can include making a list of all J sample records corresponding to samples and then making a list of all K non-duplicated reference sequences of the J samples.

Figure 3:
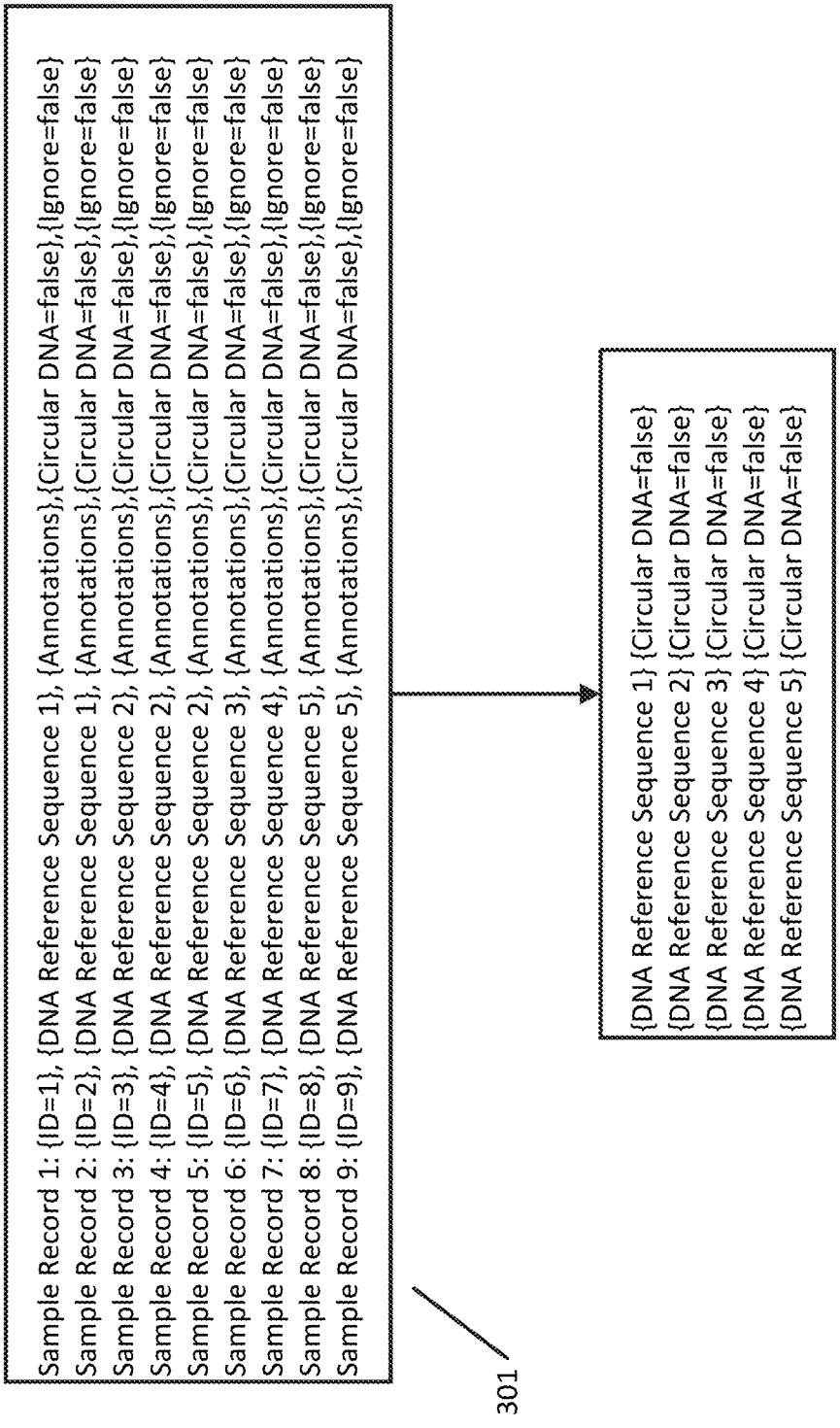
FIG. 3 illustrates an example of the step of determining a plurality of unique nucleic acid reference sequences in the plurality of sample records according to an exemplary embodiment.

FIG. 3 illustrates an example of the step of determining a plurality of unique nucleic acid reference sequences in the plurality of sample records according to an exemplary embodiment.

As shown in FIG. 3, table 301 includes nine sample records corresponding to DNA samples, each of which has a sample identifier, DNA reference sequences, annotations, a circular DNA flag, and an ignore flag. As shown in the figure, sample records 1-2 have DNA reference sequence 1, sample records 3-5 have DNA reference sequence 2, sample record 6 has DNA reference sequence 3, sample record 7 has DNA reference sequence 4, and sample records 8-9 have DNA reference sequence 5.

Table 302 shows the plurality of unique nucleic acid reference sequences in the plurality of sample records. As shown in the table, there are five unique DNA reference sequences. The circular DNA flag is also preserved for each of the unique nucleic acid reference sequences and is utilized in the overlap assessment step, as discussed below.

Returning of FIG. 2, at step 203 a plurality of nucleic acid overlaps are computed between the plurality of unique nucleic acid reference sequences. Each nucleic acid overlap corresponds to two unique nucleic acid reference sequences in the plurality of unique nucleic acid reference sequences and comprises an overlap length.

This step can include, for each pair of unique nucleic acid reference sequences in the plurality of unique nucleic acid references, determining whether an overlap exists between the pair of unique nucleic acid reference sequences by comparing the pair of unique nucleic acid reference sequences and computing the overlap length between the pair of unique nucleic acid reference sequences based at least in part on a determination that an overlap exists between the pair of unique nucleic acid reference sequences.

As discussed previously, each sample record includes a nucleic acid type variable (i.e., Circular DNA flag) and this nucleic acid type variable is set to circular (e.g., the flag is set to true) or linear (e.g., the flag is set to false). The above-mentioned step of determining whether an overlap exists between the pair of unique nucleic acid reference sequences utilizes this nucleic acid type variable to measure overlap differently between linear and circular nucleic acid sequences.

Specifically, when either of a pair of sample records corresponding to the pair of unique nucleic acid reference sequences comprise a nucleic acid type variable set to circular, then the step of determining whether an overlap exists between the pair includes comparing a circular arrangement of the pair of unique nucleic acid reference sequences. Conversely, when the pair of sample records corresponding to the pair of unique nucleic acid reference sequences both comprise a nucleic acid type variable set to linear, then the step of determining whether an overlap exists between the pair includes comparing a linear arrangement of the pair of unique nucleic acid reference sequences.

The step of computing a plurality of nucleic acid overlaps between the plurality of unique nucleic acid reference sequences requires searching for all the DNA/RNA overlaps between the plurality of unique reference sequences. This search is done by running a multi-sequence alignment (MSA) tool. This step takes as input two sets of sequences, referred to as queries and subjects. Here, both sets will correspond to the same list of 'K' reference sequences. For every pair ('q', 's') of query sequence 'q' and subject sequence 's', the MSA tool searches for DNA similarities between their nucleotide sequences. The MSA tool then reports all the found DNA aligned regions of the pair ('q', 's') and the overlap length of the found DNA regions.

The MSA tool of the present system additionally searches for circular overlaps between reference sequences as well. The result of the overlap computation step is used to determine the pooling restrictions of all the samples. Specifically, a pair of samples is going to be restricted from being pooled together if the length of any of the found DNA regions between them exceed a certain overlap threshold, as discussed below.

The system utilizes an overlap threshold, also referred to as a maximum overlap constraint, to determine whether the overlap between two reference sequences should prohibit the samples corresponding to the reference sequences from being pooled together. The maximum overlap constraint can be expressed as a maximum quantity of base pairs (bps) of the reference sequences that are permitted to overlap without requiring the samples corresponding to the reference sequences to be in separate pools. The maximum overlap constraint can be determined by the system (e.g., based on a library of sequences and differences between those sequences), input into the system by a user, and/or set to some default value. For example, maximum overlap constraint can be set to 100 bps, meaning that reference sequences that overlap by 100 base pairs or more would result in the corresponding samples from being pooled together. Optionally, the maximum overlap constraint can be algorithmically determined based on the minimum differences between reference sequences required to distinguish the reference sequences.

The maximum overlap constraint restriction is a significant constraint of the process, as not satisfying it will make the results from the mapping data analysis step unreliable. This latter assertion is true because of how the DNA/RNA fragmentation phase of NGS procedures work. In order to sequence a sample's DNA, it needs to be cut into smaller pieces (fragmentation step). So if two samples share DNA regions larger than the size of these cuts, the reads printed in the electronic file of the NGS machine cannot be assigned with certainty to one or to the other sample.

As discussed above, multiple sequence alignment (MSA) is performed on all the reference sequences prior to be submitted for sequencing. With the MSA results, the overlaps between each DNA/RNA sequence are used as input to the optimization algorithm that will then determine which ones can be pooled or mixed together. Linear Overlaps are determined by treating the DNA/RNA sequences as linear and Circular Overlaps are determined by treating the DNA/RNA sequences as circular.

Figure 4:
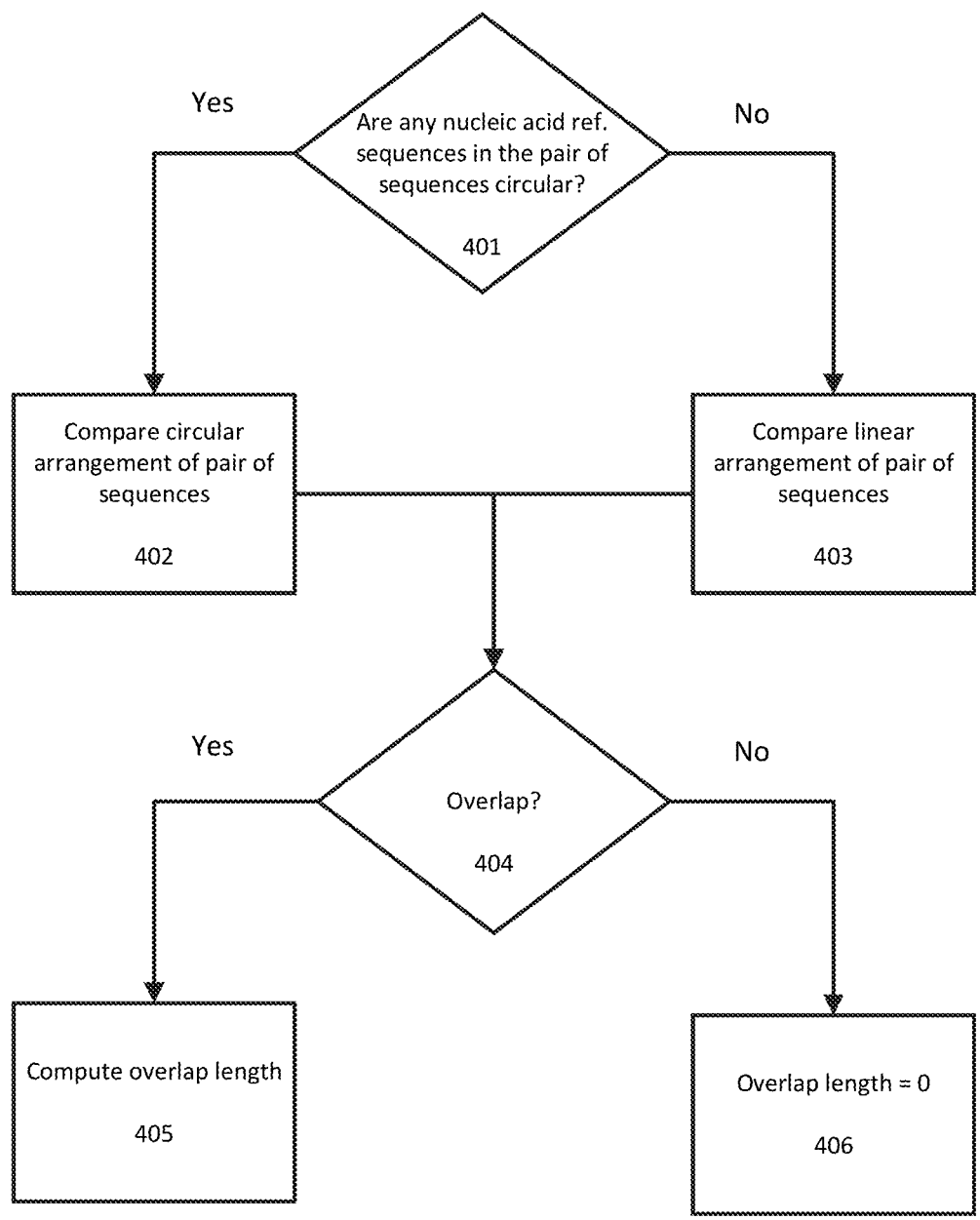
FIG. 4 illustrates a flowchart for computing a plurality of nucleic acid overlaps between the plurality of unique nucleic acid reference sequences according to an exemplary embodiment.

FIG. 4 illustrates a flowchart for computing a plurality of nucleic acid overlaps between the plurality of unique nucleic acid reference sequences according to an exemplary embodiment. The steps shown in FIG. 4 are performed for each pair of unique nucleic acid reference sequences in the plurality of unique nucleic acid reference sequences. For example, if there were three unique nucleic acid reference sequences (1, 2, and 3), then the steps of FIG. 4 would be performed for (1+2), (1+3), and (2+3).

At step 401 it is determined whether any of the unique nucleic acid reference sequences in the pair of unique nucleic acid reference sequences are circular. This can be determined by checking the nucleic acid type variable (i.e. the CircularDNA variable) for the sample records corresponding to the pair of unique nucleic acid reference sequences.

If any of sequences are circular, then at step 402 a circular arrangement of the pair of reference sequences is compared. If both of the sequences are not circular, then at step 403 a linear arrangement of the pair of reference sequences is compared.

At step 404 a determination is made regarding whether there is any overlap between the pair of reference sequences. If there is overlap, then at step 405 the overlap length is computed. If there is no overlap then at step 406 the overlap length is set to zero.

It is important to make the distinction between circular and linear nucleic acid sequences and recognize which samples have circular DNA (e.g., bacterial plasmids). Since circular DNA has no end or beginning, the overlap analyses must take this into consideration. The presented algorithm improves traditional MSA tools and correctly handles circular DNA alignments.

Figure 5:
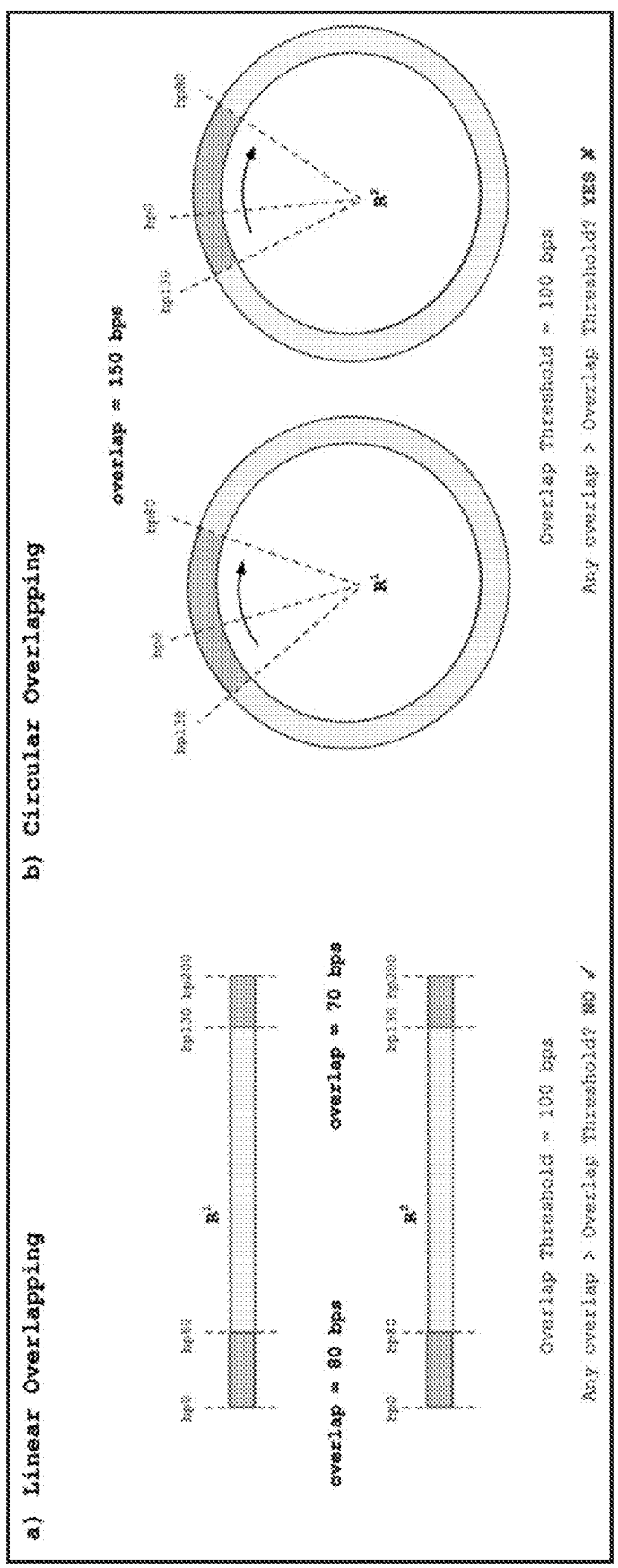
FIG. 5 illustrates an example of the circular and linear overlap determination according to an exemplary embodiment.

FIG. 5 illustrates an example of the circular and linear overlap determination according to an exemplary embodiment. The figure shows the overlaps between reference sequences R1 and R2 with different circular DNA. Green areas are overlapping regions, while gray areas are non-overlapping regions. Section a (on the left hand side) shows the computation of linear overlapping between the two reference sequences and section b shows the computation of circular overlapping between the two reference sequences. In both cases the Overlap Threshold (i.e., the maximum overlap constraint) equals 100 nucleotide base pairs (100 bps). In the case of linear overlapping, two overlaps are found at each linear sequence extremes, each of them below the threshold of 100 bps, with 80 bps and 70 bps respectively. In the case of circular overlapping, one overlap is found exceeding the 100 bps restriction threshold. This demonstrates that since the reference sequences are circular, treating them as linear can falsely satisfy the overlap restriction.

In order to compute DNA/RNA overlaps, multiple sequence linear alignments (MSA) are performed on all pairs of reference sequences in the reference sequences submitted for sequencing. The linear MSA results and circular MSA are then processed and used to determine an optimal grouping, as explained below.

Returning to FIG. 2, at step 204 an optimal grouping of the plurality of samples into a plurality of sample pools is determined based at least in part on the nucleic acid reference sequence of each sample record, the plurality of nucleic acid overlaps between the plurality of unique nucleic acid reference sequences, and one or more constraints, the one or more constraints including the maximum overlap constraint.

As explained below, this step determines a solution space to define an optimization problem that can be solved efficiently. The optimization variables of the defined solution space are then iteratively optimized by the algorithm until the optimization's objective is maximized and all constraints are satisfied.

The optimal grouping has the minimum quantity of sample pools required to sequence all of the samples and also complies with the maximum overlap constraint to ensure that all samples which have corresponding reference sequences exceeding the maximum overlap constraint are not pooled together. A consequence of the maximum overlap constraint is that every pool will have samples that have different reference sequences (i.e., no duplicate reference sequences). The optimal grouping defines which samples belong in which pool and can be utilized to perform the required sequencing in an efficient manner.

In the optimal grouping, the overlap length between any two nucleic acid reference sequences of any two samples within each sample pool does not exceed the maximum overlap constraint. Additionally, the quantity of sample pools in the optimal grouping comprises a minimum quantity of sample pools required for grouping the plurality of samples while complying with the one or more constraints (including the maximum overlap constraint). As discussed previously, the one or more constraints can be set to some default value, input by a user, or automatically determined based on the specific sequences within the samples.

An additional constraint that can be utilized to determine the optimal grouping is a maximum pool size constraint that limits the quantity of samples that can be placed in a single pool. The maximum pool size constraint can be provided as input by the user and/or set to some default value and ensures that the sample pool size of the sample pools is not so large that it cannot be sequenced by the NGS machines. Another constraint is a requirement that all samples must be assigned to a pool (unless an ignore flag has been set for the sample record).

Figure 6:
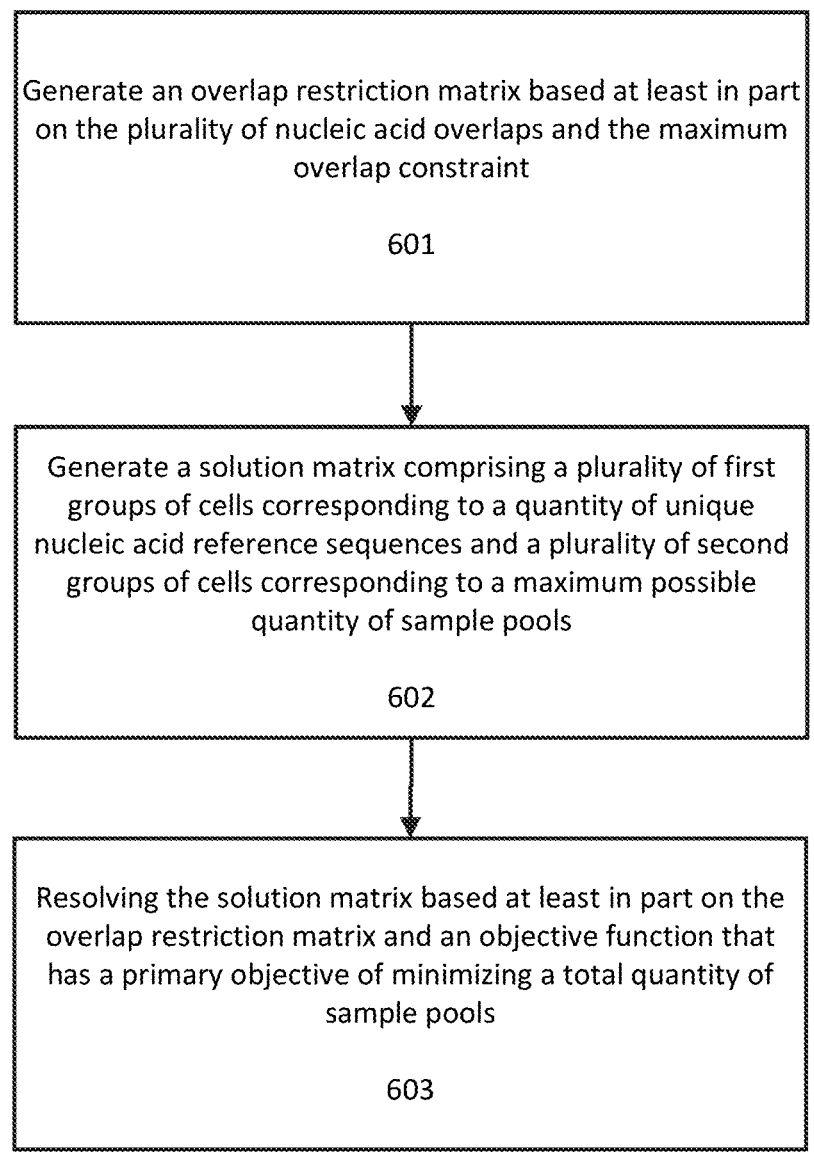
FIG. 6 illustrates a flowchart for determining an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints according to an exemplary embodiment.

FIG. 6 illustrates a flowchart for determining an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints according to an exemplary embodiment.

At step 601 an overlap restriction matrix is generated based at least in part on the plurality of nucleic acid overlaps and the maximum overlap constraint. Each cell of the overlap restriction matrix corresponds to a pair of unique nucleic acid reference sequences and indicates whether the overlap length between the pair of unique nucleic acid reference sequences exceeds the maximum overlap constraint.

As discussed earlier, the system searches for all the DNA overlaps between the unique reference sequences of all of samples. The result of this step is a 'K by K' numerical matrix (referred to here as the overlap restriction matrix). Every cell of this matrix corresponds to pair ('q', 's') of query sequence 'q' and subject sequence 's'. Each cell (kq, ks) of this matrix corresponds to a binary value (true or false), that will be true if the (kq, ks) sequence pair have overlapping DNA regions above the overlap threshold (maximum overlap constraint), and false if they do not.

This matrix is always diagonal with diagonal cells equal to 1, meaning that all reference sequences evidently exceed the overlap threshold when aligned to themselves (as they are identical). Moreover, the matrix is always symmetric with cells (kq, ks) equal to (ks, kq), meaning that the DNA regions found between reference sequence 'q' and 's', are the same found between 's' and 'q'.

Figure 7:
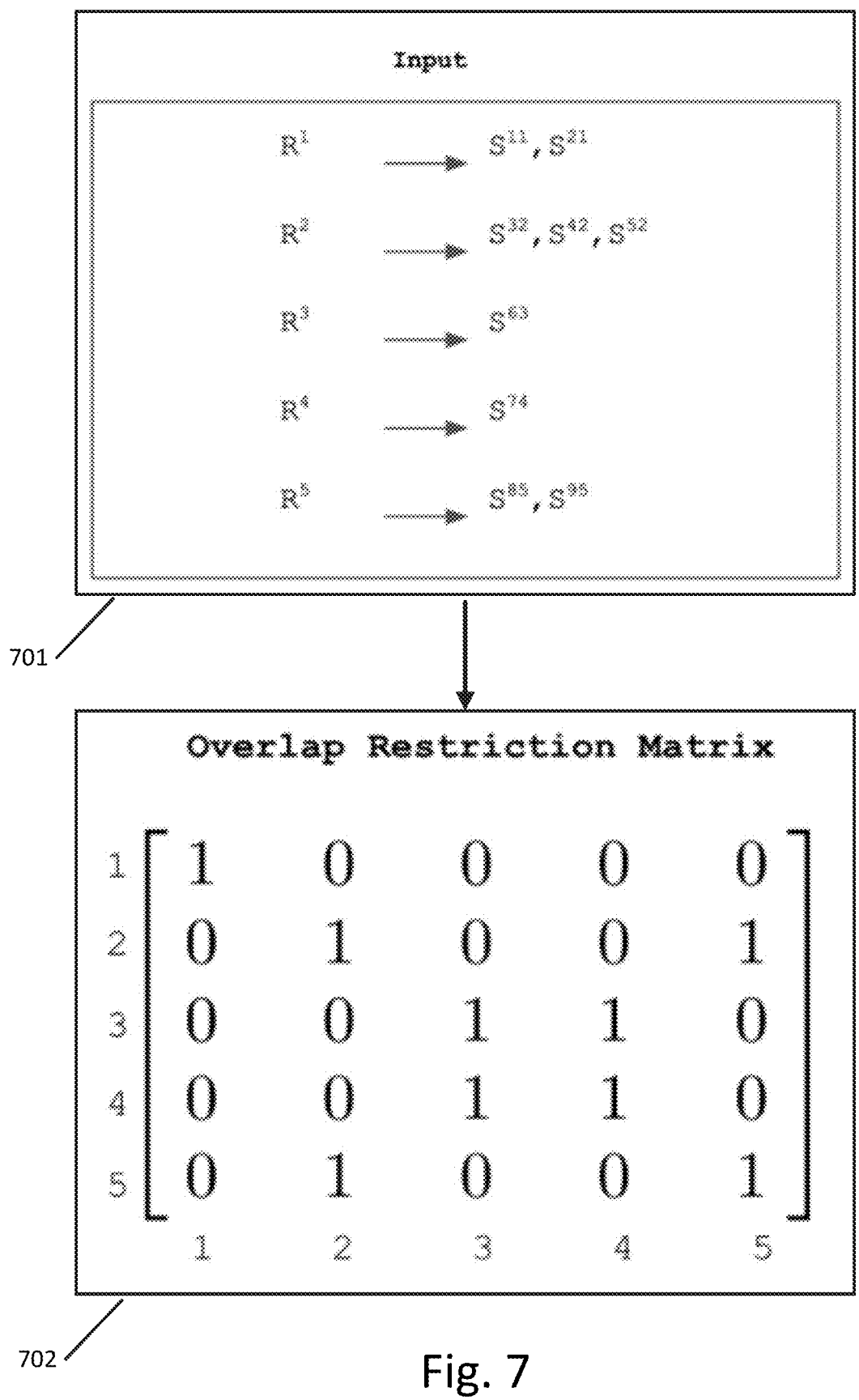
FIG. 7 illustrates an example of an overlap restriction matrix according to an exemplary embodiment.

FIG. 7 illustrates an example of an overlap restriction matrix according to an exemplary embodiment. Box 701 illustrates a sample input having 9 samples with five different reference sequences. Here the five reference sequences span 2, 3, 1, 1 and 2 samples respectively. For example, reference sequence 3 corresponds to sample 6. All samples have distinct 'j' indexes, but those coming from the same reference share their 'k' index accordingly.

Box 702 an example of a possible overlap restriction matrix based on the input in box 701. As shown in FIG. 7, the diagonal cells are all 1 as explained above. Here, the reference sequence pairs (2,5) and (3,4) are said to exceed the overlap threshold, thus their spanned samples cannot be pooled together. This matrix is always symmetric and always diagonal, thus cells (i,j)=(j,i) and (i,i)=1

Returning to FIG. 6, at step 602 a solution matrix comprising a plurality of first groups of cells corresponding to a quantity of unique nucleic acid reference sequences and a plurality of second groups of cells corresponding to a maximum possible quantity of sample pools is generated. Each first group of cells in the solution matrix corresponds to a unique nucleic acid reference and each second group of cells corresponds to a potential sample pool. The total quantity of second groups (i.e., potential sample pools) will be equal to the total number of samples and reflects the worst-case scenario where each sample must be assigned to its own pool.

The plurality of first groups can correspond to a plurality of columns of cells in the solution matrix and the plurality of second groups can correspond to a plurality of rows of cells. Alternatively, the rows and columns can be switched so that the plurality of first groups can correspond to a plurality of rows of cells in the solution matrix and the plurality of second groups can correspond to a plurality of columns of cells.

The step of generating a solution matrix defines the solution space of the optimization problem. An 'M by K' binary matrix (herein referred here as the solution matrix) is created, where 'M' and 'K' represent the total number of possible pools, and the total number of non-duplicated reference sequences respectively. The cells of this matrix represent all the optimization variables. The values these cell variables may take is binary (0 or 1). A given cell variable (m, k) taking a value of 1 means that a sample with reference sequence Rk belongs to pool Pm. Recall that a reference sequence R may correspond to the reference sequence of one or multiple samples. The solution matrix is the solution space of the optimization, so during the optimization, the program will iteratively modify the binary state of each cell variable until the optimization's objective is maximized and the following constraints are satisfied.

The constraints of the optimization problem are discussed above and described again below:

Overlap constraint: This uses the overlap restriction matrix described previously, to create the overlap constraints of the optimization problem. These constraints restricts a pool from containing samples with similar DNA regions. This constraint is fundamental because otherwise it would not be possible to map the pools' DNA fragments back to their corresponding reference sequences.

Row constraints on the solution matrix: If the optional maximum pool size constraint is utilized, the sum of each row 'm' needs to be less than or equal to the optional maximum pool size constraint provided as input. Each cell value of the solution matrix is binary (1 or 0) and each row represents a pool of reference sequences that do not break the overlap constraint. Each reference sequence maps to a sample, so the sum of the row 'm' represents the number of samples of pool Pm.

Column restrictions on the solution matrix: The sum of each column 'k' must be strictly equal to the number of samples sharing the same reference sequence Rk. This forces to place all samples with reference sequence Rk into different pools. Also this avoids the optimization from leaving samples with no pool assigned. Also, samples with the same reference sequence will never be together in the same pool.

FIG. 8 illustrates an example of a solution matrix according to an exemplary embodiment. All 'x' elements in the solution matrix correspond to the binary optimization variables. In this example, rows represent pools 'P' and columns represent the distinct reference sequences 'R'.

Returning to FIG. 6, at step 603 the solution matrix is resolved based at least in part on the overlap restriction matrix and an objective function that has a primary objective of minimizing a total quantity of sample pools. The solution matrix can be resolved based at least in part on one or more additional constraints, including the constraints discussed above, such as the column restrictions and the maximum pool size constraint.

As previously explained, the goal of the optimization is to accomplish the best possible reduction in the number of final pools (sequencing elements) while forcing all samples to be inserted in some pool. The objective function is configured to generate this result. Optimizing the objective function incentivizes the optimization solution towards decreasing the number of pools to pool as many samples together as possible. To fulfill this purpose, the objective function results in a higher score when samples are pooled together with as many other samples as possible.

By using the solution matrix of this particular implementation, the objective function must incentivize the optimization towards increasing the number of "empty-rows", in other words, attain as much empty-rows or zero-sum rows as possible. To fulfill this purpose, a scoring technique is used, which gives higher scores to samples positioned at the top rows as to those positioned in bottom ones. Then, the optimization is to maximize the sum of each sample's score. This means that the optimization process will try to push as many samples as possible into the top rows, leaving much of the bottom rows empty.

FIG. 9 illustrates an example of a resolved solution matrix according to an exemplary embodiment. As can be seen from the figure, rows 6-9 (corresponding to potential sample pools 6-9) do not contain any samples (they do not contain any reference sequences). Only the non-empty rows are used as the final sample pools in the final distribution of the plurality of samples, while the empty rows are discarded or ignored. The solution matrix is shown resolved based on the constraints previously discussed, although no maximum pool size constraint was used. The reduction attained in this example is 5/9 (55.55%), with 4 empty rows.

The step of determining an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints can further include balancing a quantity of samples in each sample pool in the resolved solution matrix.

In this implementation, once the algorithm minimizes the number of sequencing elements or pools, it runs a second balancing optimization step. This means that in addition to minimizing the number of pools, it also balances the number samples per pool across all pools. This balancing is important because NGS machines usually read a relatively fixed amount of DNA material per sequencing element or pool. Thus, pools with more DNA material have less chance to get all their DNA fragments read with the same confidence level than pools with lesser DNA material. Balancing improves the base pair call statistics for all the sequenced samples.

After the pool minimization (i.e., solution resolving) is finished, the solution matrix is used as input for the balancing optimization. This optimization runs with the objective of balancing the sum of the non-empty rows of the solution matrix. In other words, it minimizes the variance of the sum of non-empty rows of the solution matrix, while maintaining the number of empty rows found in the resolving step and satisfying the constraints given by the overlap restriction matrix.

FIG. 10 illustrates an example of pool balancing according to an exemplary embodiment. Solution matrix 1000 shows the solution matrix after the resolving step. Solution matrix 1001 shows the solution matrix after the pool balancing optimization step. It can be observed from matrix 1001 that sample $S^{11}$ was moved from row 1 to row 3, and sample $S^{22}$ was moved from row 2 to row 4. After balancing, the solution matrix ends up with 4 two-element pools and 1 single-element pool, thereby reducing the variance of the sums of its rows.

The resolved solution matrix indicates a number of equivalent solutions for the final distribution of the plurality of samples in sample pools. After the completion of all of the described steps, the samples can be grouped into their pools according to the solution matrix rows matrix 1000 or the balanced solution matrix 1001. This step explained below using the balanced solution matrix 1001.

The first row of the solution matrix represents Pool 1, which indicates that any two distinct samples with reference sequences R2 and R3 can be put together. The second row represents Pool 2 and indicates that any two distinct samples with reference sequences R1 and R4 can be grouped. The third row represents Pool 3 and indicates that any two distinct samples with reference sequences R1 and R2 can be pooled together. The fourth row represents Pool 4 and indicates that any two distinct samples with reference sequences R2 and R5 can be pooled. Finally, the fifth row represents Pool 5 and indicates that any sample with reference sequence R5 must have its own pool.

It is important to note that the solution matrix does not specify which sample goes in what pool, but rather indicates which of the reference sequences should be pooled. Actual samples for pooling can be determined from this because there is no need to distinguish between samples with the same reference sequence. This can be done with a step that pools the actual samples based upon the instructions/requirements of the resolved/balanced solution matrix. This is accomplished by taking samples from an ordered list according to their reference sequences and building the sample pools in the manner specified by the solution matrix.

Using the example input 701 in FIG. 7 and the balanced solution matrix 1001 in FIG. 10, the result of this step would be:

Pool 1: ($S^{32}$, $S^{63}$)
Pool 2: ($S^{21}$, $S^{74}$)
Pool 3: ($S^{11}$, $S^{52}$)
Pool 4: ($S^{42}$, $S^{85}$)
Pool 5: ($S^{95}$)

This solution is identical from an optimization standpoint to the following alternative, in which samples $S^{11}$ with $S^{21}$ got swapped:

Pool 1: $(S^{32}, S^{63})$
Pool 2: $(S^{11}, s^{74})$
Pool 3: $(S^{21}, S^{32})$
Pool 4: $(S^{42}, S^{85})$
Pool 5: $(S^{95})$ As long as the swapped samples have the same reference sequence (represented by secondary superscript) any alternative solution will be optimally identical.

Once the solution is determined, then the resulting sample groups can be utilized. This can take the form of providing, transmitting, or generating instructions to a user or a lab regarding which samples should be pooled. Returning to FIG. 2, at step 205 an electronic file or printed document comprising the plurality of sample pools of the optimal grouping is generated, with each sample pool identifying one or more samples in the sample pool. Once the solution is found (i.e., the solution matrix is resolved), the program will go through a parsing phase with the relevant inputs (i.e., the sample records) and write the final results into the electronic file/printed document with the information of how samples are pooled. For example, the results can be parsed an electronic file, such as a JavaScript Object Notation (JSON) file, containing each sample ID linked to a Pool ID. The end user can then turn these results into instructions on how to pool the original samples prior to the sequencing process in the laboratory.

The laboratory users/technicians can then pool the samples as indicated by the electronic file and provide the sample pools to a next generation sequencing machine, as required for sequencing.

The disclosed system can include one or more next generation sequencing machines for sequencing the samples. At step 206 the one or more next generation sequencing machines are used to sequence one or more sample pools in the plurality of sample pools of the optimal grouping and output/transmit the results of the sequencing. This step can be repeated until all of the samples pools of the optimal grouping are sequenced.

After sequencing, the output of the NGS machine can be used to validate the reference sequences of the samples. As explained previously, reference sequences can correspond to the DNA or RNA sequence that was intended to be designed or created in a specific sample. The sequencing step can confirm that the correct sequence was created.

Figure 11:
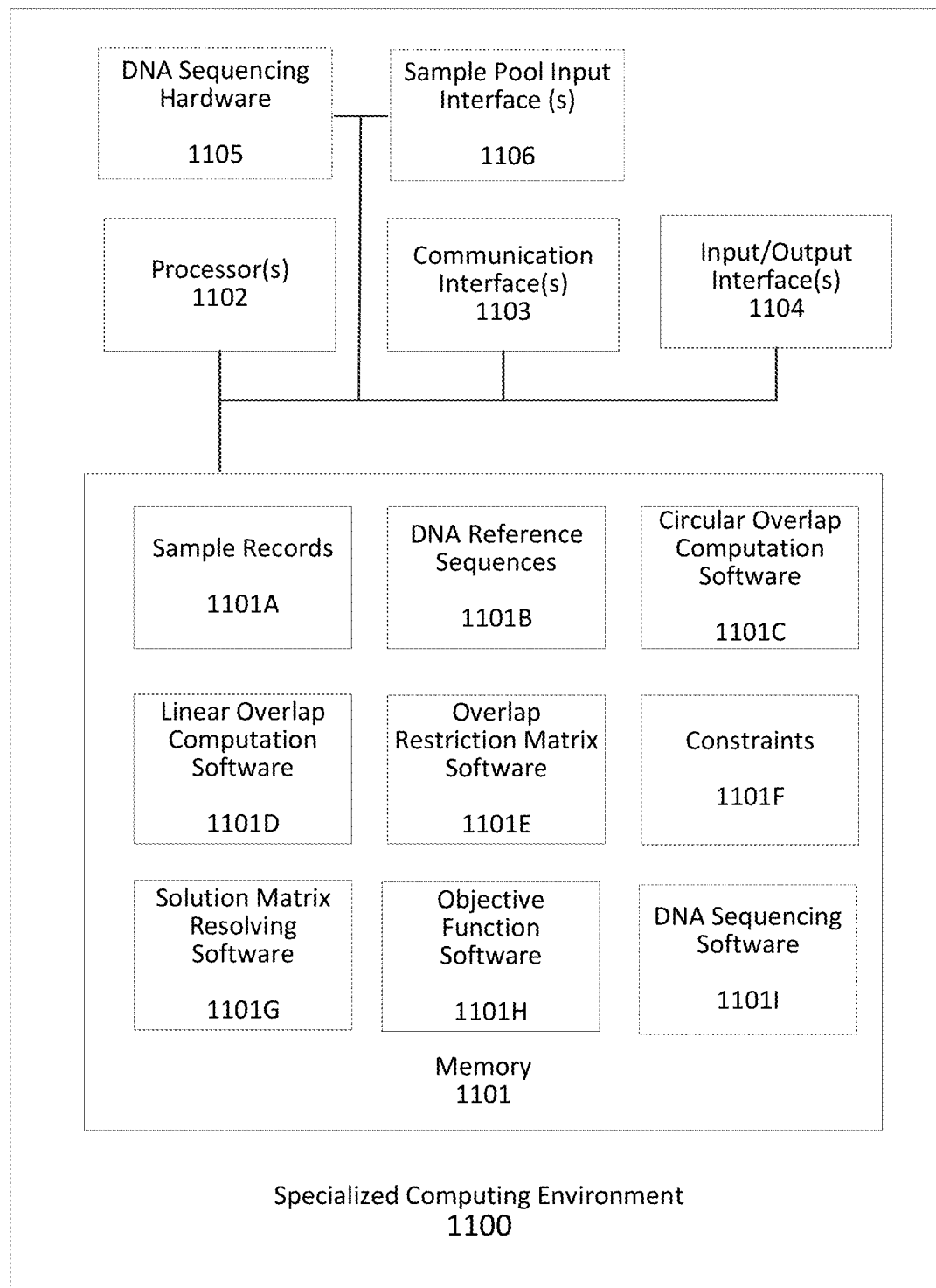
FIG. 11 illustrates the components of the specialized computing environment for optimal pooling of nucleic acid samples for next generation sequencing.

FIG. 11 illustrates the components of the specialized computing environment 1300 for optimal pooling of nucleic acid samples for next generation sequencing. Specialized computing environment 1100 can be made up of one or more computing devices that include a memory 1101 that is a non-transitory computer-readable medium and can be volatile memory (e.g., registers, cache, RAM), non-volatile memory (e.g., ROM, EEPROM, flash memory, etc.), or some combination of the two.

As shown in FIG. 11, memory 1101 can store sample records 1101A, DNA reference sequences 1101B, circular overlap computation software 1101C, linear overlap computation software 1101D, overlap restriction matrix software 1101E, constraints 1101F, solution matrix generation and resolving software 1101G, and objective function software 1101H. Optionally, when the system includes NGS machines, the memory 1101 can also store DNA/RNA sequencing software 1101I.

Each of the software components in memory 1101 store specialized instructions and data structures configured to perform the methods for optimal pooling of nucleic acid samples for next generation sequencing described herein.

All of the software stored within memory 1101 can be stored as a computer-readable instructions, that when executed by one or more processors 1102, cause the processors to perform the functionality described with respect to FIGS. 1-10.

Processor(s) 1102 execute computer-executable instructions and can be a real or virtual processors. In a multi-processing system, multiple processors or multicore processors can be used to execute computer-executable instructions to increase processing power and/or to execute certain software in parallel. As discussed earlier in the application, processors can be processors specialized for parallel processing or optimization, such as graphical processing units (GPUs).

Computing environment 1100 additionally includes a communication interface 1103, such as a network interface, which is used to communicate with devices, applications, or processes on a computer network or computing system, collect data from devices on a network, and implement encryption/decryption actions on network communications within the computer network or on data stored in databases of the computer network. The communication interface conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Computing environment 1100 further includes input and output interfaces 1104 that allow users (such as system administrators) to provide input to the system, edit data stored in memory 1101, or to perform other administrative functions. For example, an administrator can configure, add, or edit, for example, constraints 1101F or sample records 1101A.

An interconnection mechanism (shown as a solid line in FIG. 11), such as a bus, controller, or network interconnects the components of the computing environment 1100.

Input and output interfaces 1104 can be coupled to input and output devices. For example, Universal Serial Bus (USB) ports can allow for the connection of a keyboard, mouse, pen, trackball, touch screen, or game controller, a voice input device, a scanning device, a digital camera, remote control, or another device that provides input to the computing environment.

The computing environment 1100 can additionally utilize a removable or non-removable storage, such as magnetic disks, magnetic tapes or cassettes, CD-ROMs, CD-RWs, DVDs, USB drives, or any other medium which can be used to store information and which can be accessed within the computing environment 1100.

Computing environment 1100 can be a set-top box, personal computer, or one or more servers, for example a farm of networked servers, a clustered server environment, or a cloud network of computing devices. Optionally, when the system includes NGS machines, the computing environment 1100 can include DNA sequencing hardware 1105 and a sample pool input interface 1106.

The novel method, apparatus, and computer-readable medium for optimal pooling of nucleic acid samples for next generation sequencing disclosed herein provides several technical advantages and technical effects that improve the performance and efficiency of computing devices and next generation sequencing machines.

FIG. 12 illustrates a table with experimental results showing the specific technical advantages and improvements of the present system relative to previous systems. Table 1200 is a comparative table of the machine time and monetary costs of the different alternatives available for DNA/RNA sequencing.

The specific task (Task A) for this evaluation required sequencing of 200 samples with 50 unique reference sequences, having a maximum tuple size of 5, and overlap threshold of 100 base pairs, and no annotations (meaning every part of the reference sequence is inspected for DNA region similarities). The unique reference sequences used for this Task were retrieved from the first 50 results of the NCBI (National Center for Biotechnology) Nucleotide database.

"3000:10000 [Sequence Length] AND "Clostridium" [Organism] DNA"

As shown in table 1200, three alternatives are evaluated. Alternative a is the sequencing of samples individually without multiplexing. Alternative b is sequencing of samples with manual multiplexing. This involves manually inspecting the DNA similarities and overlaps between the reference sequences of the samples with a DNA alignment tool and grouping the samples. Alternative c is sample multiplexing using the present system for optimal pooling of nucleic acid samples for next generation sequencing.

For alternative b (manual sample multiplexing) analysis, it is assumed that a human is capable of successfully finding the best way of grouping the 200 samples in groups of 2 (groups of higher size are unattainable by means of simple human inspection). This is a highly optimistic, but assumed possible for the purpose of this example. The Man Hours needed (M/H) for alternative b are estimated to be a full-time work day. However, this may also be underestimated due to the tediousness of manually grouping samples by inspecting all of their DNA similarities on a 50 by 50 matrix. The hardware specifications of the machine used to compute the table shown in FIG. 12 is 2.2 GHZ Intel Core i7 with 16 GB of RAM. Additionally, the M/H costs were estimated using the average yearly net income of a Biotech Engineer in the US to be 71,919 USD, resulting in a full-time work day of 8 hours costing 205.2 USD. Monetary costs are calculated on a 5.9 USD per sample estimation. This is the approximate cost of sequencing a single sample with a particular NGS Machine. This cost accounts for the costs of the sample library preparation steps mentioned above (mainly fragmentation and amplification), NGS machine sequencing biokits and time costs of using the machine.

As shown in FIG. 12, the novel method and system for optimal pooling of nucleic acid samples for next generation sequencing results in improved efficiency (in both man hours and in machine efficiency), reduced time, and reduced costs compared to other sequencing methods. Significantly, the present system and method (alternative c) not only reduce the man hours and man hour cost, but improve the efficiency of the next generation sequencing machine when sequencing the same 200 sample data set. Specifically, the machine time required for the present method was less than three minutes, compared with approximately 5 minutes for manual sample multiplexing and the number of sequencing elements is reduced from 100 sequencing elements to 60 sequencing elements.

Additionally, the present system and method enable more sophisticated multiplexing than could be performed manually. The present system can be used to group samples into large sample pools (sequencing elements) which is not possible through manual inspection.

The present system and method also has advantages over the barcoding method of multiplexing, which is typically utilized for large numbers of samples (>1,000). Unlike barcoding, the disclosed method does not require the steps of designing and synthesizing individual DNA barcodes, performing additional DNA ligation steps, and then performing a computational demultiplexing step to map the sequenced fragment to the original sample library, all of which come with significant time and economic costs.

It will be appreciated by those skilled in the art that changes could be made to the embodiments described above without departing from the broad inventive concept thereof. For example, the steps or order of operation of one of the above-described methods could be rearranged or occur in a different series, as understood by those skilled in the art. It is understood, therefore, that this disclosure is not limited to the particular embodiments disclosed, but it is intended to cover modifications within the spirit and scope of the following claims.

The invention claimed is:

1. A method executed by one or more computing devices comprising at least one next generation sequencing machine for optimal pooling of nucleic acid samples for next generation sequencing, the method comprising:
    receiving, by at least one of the one or more computing devices, a plurality of sample records comprising an electronic representation of a plurality of samples, each sample record comprising a sample identifier and a nucleic acid reference sequence of the sample;
    determining, by at least one of the one or more computing devices, a plurality of unique nucleic acid reference sequences in the plurality of sample records;
    computing, by at least one of the one or more computing devices, a plurality of nucleic acid overlaps between the plurality of unique nucleic acid reference sequences, wherein each nucleic acid overlap corresponds to two unique nucleic acid reference sequences in the plurality of unique nucleic acid reference sequences and comprises an overlap length;
    determining, by at least one of the one or more computing devices, an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints, the one or more constraints comprising a maximum overlap constraint, wherein the overlap length between any two nucleic acid reference sequences of any two samples within each sample pool does not exceed the maximum overlap constraint and wherein a quantity of sample pools in the optimal grouping comprises a minimum quantity of sample pools required for grouping the plurality of samples while complying with the one or more constraints; and
    sequencing, by the at least one next generation sequencing machine in the one or more computing devices, one or more sample pools in the plurality of sample pools of the optimal grouping.

2. The method of claim 1, wherein computing the plurality of nucleic acid overlaps between the plurality of unique nucleic acid reference sequences comprises, for each pair of unique nucleic acid reference sequences in the plurality of unique nucleic acid reference sequences:

determining whether an overlap exists between the pair of unique nucleic acid reference sequences by comparing the pair of unique nucleic acid reference sequences; and computing the overlap length between the pair of unique nucleic acid reference sequences based at least in part on a determination that an overlap exists between the pair of unique nucleic acid reference sequences.

3. The method of claim 2, wherein each sample record comprises a nucleic acid type variable, the nucleic acid type variable being set to either circular or linear and wherein determining whether an overlap exists between the pair of unique nucleic acid reference sequences by comparing the pair of unique nucleic acid reference sequences comprises:

comparing a circular arrangement of the pair of unique nucleic acid reference sequences when either of a pair of sample records corresponding to the pair of unique nucleic acid reference sequences comprise a nucleic acid type variable set to circular; or comparing a linear arrangement of the pair of unique nucleic acid reference sequences when the pair of sample records corresponding to the pair of unique nucleic acid reference sequences both comprise a nucleic acid type variable set to linear.

4. The method of claim 1, wherein determining an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints comprises:

generating an overlap restriction matrix based at least in part on the plurality of nucleic acid overlaps and the maximum overlap constraint, each cell of the overlap restriction matrix corresponding to a pair of unique nucleic acid reference sequences and indicating whether the overlap length between the pair of unique nucleic acid reference sequences exceeds the maximum overlap constraint;

generating a solution matrix comprising a plurality of first groups of cells corresponding to a quantity of unique nucleic acid reference sequences and a plurality of second groups of cells corresponding to a maximum possible quantity of sample pools, wherein each first group of cells corresponds to a unique nucleic acid reference and wherein each second group of cells corresponds to a potential sample pool; and resolving the solution matrix based at least in part on the overlap restriction matrix and an objective function that has a primary objective of minimizing a total quantity of sample pools.

5. The method of claim 4, wherein the plurality of first groups correspond to a plurality of columns of cells in the solution matrix and the plurality of second groups correspond to a plurality of rows of cells.

6. The method of claim 4, wherein determining the optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints comprises:

balancing a quantity of samples in each sample pool in the resolved solution matrix.

7. The method of claim 4, wherein the one or more constraints comprise a maximum pool size constraint and wherein the solution matrix is resolved based at least in part on the maximum pool size constraint.

8. The method of claim 1, further comprising:

generating, by at least one of the one or more computing devices, an electronic file comprising the plurality of sample pools of the optimal grouping, each sample pool identifying one or more samples in the sample pool.

9. An apparatus for optimal pooling of nucleic acid samples for next generation sequencing, the apparatus comprising:

at least one next-generation sequencing machine;
one or more processors; and
one or more memories operatively coupled to at least one of the one or more processors and having instructions stored thereon that, when executed by at least one of the one or more processors, cause at least one of the one or more processors to:

receive a plurality of sample records comprising an electronic representation of a plurality of samples, each sample record comprising a sample identifier and a nucleic acid reference sequence of the sample;

determine a plurality of unique nucleic acid reference sequences in the plurality of sample records;

compute a plurality of nucleic acid overlaps between the plurality of unique nucleic acid reference sequences, wherein each nucleic acid overlap corresponds to two unique nucleic acid reference sequences in the plurality of unique nucleic acid reference sequences and comprises an overlap length;

determine an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints, the one or more constraints comprising a maximum overlap constraint, wherein the overlap length between any two nucleic acid reference sequences of any two samples within each sample pool does not exceed the maximum overlap constraint and wherein a quantity of sample pools in the optimal grouping comprises a minimum quantity of sample pools required for grouping the plurality of samples while complying with the one or more constraints; and sequence, with the at least one next generation sequencing machine of the apparatus, one or more sample pools in the plurality of sample pools of the optimal grouping.

10. The apparatus of claim 9, wherein the instructions that, when executed by at least one of the one or more processors, cause at least one of the one or more processors to compute a plurality of nucleic acid overlaps between the plurality of unique nucleic acid reference sequences further cause at least one of the one or more processors to, for each pair of unique nucleic acid reference sequences in the plurality of unique nucleic acid reference sequences:

determine whether an overlap exists between the pair of unique nucleic acid reference sequences by comparing the pair of unique nucleic acid reference sequences; and compute the overlap length between the pair of unique nucleic acid reference sequences based at least in part on a determination that an overlap exists between the pair of unique nucleic acid reference sequences.

11. The apparatus of claim 10, wherein each sample record comprises a nucleic acid type variable, the nucleic acid type variable being set to either circular or linear and wherein the instructions that, when executed by at least one of the one or more processors, cause at least one of the one or more processors to determine whether an overlap exists between the pair of unique nucleic acid reference sequences by comparing the pair of unique nucleic acid reference sequences further cause at least one of the one or more processors to:
- compare a circular arrangement of the pair of unique nucleic acid reference sequences when either of a pair of sample records corresponding to the pair of unique nucleic acid reference sequences comprise a nucleic acid type variable set to circular; or
- compare a linear arrangement of the pair of unique nucleic acid reference sequences when the pair of sample records corresponding to the pair of unique nucleic acid reference sequences both comprise a nucleic acid type variable set to linear.

12. The apparatus of claim 9, wherein the instructions that, when executed by at least one of the one or more processors, cause at least one of the one or more processors to determine an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints further cause at least one of the one or more processors to:
- generate an overlap restriction matrix based at least in part on the plurality of nucleic acid overlaps and the maximum overlap constraint, each cell of the overlap restriction matrix corresponding to a pair of unique nucleic acid reference sequences and indicating whether the overlap length between the pair of unique nucleic acid reference sequences exceeds the maximum overlap constraint;
- generate a solution matrix comprising a plurality of first groups of cells corresponding to a quantity of unique nucleic acid reference sequences and a plurality of second groups of cells corresponding to a maximum possible quantity of sample pools, wherein each first group of cells corresponds to a unique nucleic acid reference and wherein each second group of cells corresponds to a potential sample pool; and
- resolve the solution matrix based at least in part on the overlap restriction matrix and an objective function that has a primary objective of minimizing a total quantity of sample pools.

13. The apparatus of claim 12, wherein the plurality of first groups correspond to a plurality of columns of cells in the solution matrix and the plurality of second groups correspond to a plurality of rows of cells.

14. The apparatus of claim 12, wherein the instructions that, when executed by at least one of the one or more processors, cause at least one of the one or more processors to determine an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints further cause at least one of the one or more processors to:
- balance a quantity of samples in each sample pool in the resolved solution matrix.

15. The apparatus of claim 12, wherein the one or more constraints comprise a maximum pool size constraint and wherein the solution matrix is resolved based at least in part on the maximum pool size constraint.

16. The apparatus of claim 9, wherein at least one of the one or more memories has further instructions stored thereon that, when executed by at least one of the one or more processors, cause at least one of the one or more processors to:
- generate an electronic file comprising the plurality of sample pools of the optimal grouping, each sample pool identifying one or more samples in the sample pool.

17. At least one non-transitory computer-readable medium for optimal pooling of nucleic acid samples for next generation sequencing, the at least one non-transitory computer-readable medium storing computer-readable instructions that, when executed by one or more computing devices comprising at least one next generation sequencing machine, cause at least one of the one or more computing devices to:
- receive a plurality of sample records comprising an electronic representation of a plurality of samples, each sample record comprising a sample identifier and a nucleic acid reference sequence of the sample;
- determine a plurality of unique nucleic acid reference sequences in the plurality of sample records;
- compute a plurality of nucleic acid overlaps between the plurality of unique nucleic acid reference sequences, wherein each nucleic acid overlap corresponds to two unique nucleic acid reference sequences in the plurality of unique nucleic acid reference sequences and comprises an overlap length;
- determine an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints, the one or more constraints comprising a maximum overlap constraint, wherein the overlap length between any two nucleic acid reference sequences of any two samples within each sample pool does not exceed the maximum overlap constraint and wherein a quantity of sample pools in the optimal grouping comprises a minimum quantity of sample pools required for grouping the plurality of samples while complying with the one or more constraints; and
- sequence, with the at least one next generation sequencing machine in the one or more computing devices, one or more sample pools in the plurality of sample pools of the optimal grouping.

18. The at least one non-transitory computer-readable medium of claim 17, wherein the instructions that, when executed by at least one of the one or more computing devices, cause at least one of the one or more computing devices to compute a plurality of nucleic acid overlaps between the plurality of unique nucleic acid reference sequences further cause at least one of the one or more computing devices to, for each pair of unique nucleic acid reference sequences in the plurality of unique nucleic acid reference sequences:
- determine whether an overlap exists between the pair of unique nucleic acid reference sequences by comparing the pair of unique nucleic acid reference sequences; and
- compute the overlap length between the pair of unique nucleic acid reference sequences based at least in part on a determination that an overlap exists between the pair of unique nucleic acid reference sequences.

19. The at least one non-transitory computer-readable medium of claim 18, wherein each sample record comprises a nucleic acid type variable, the nucleic acid type variable being set to either circular or linear and wherein the instructions that, when executed by at least one of the one or more computing devices, cause at least one of the one or more computing devices to determine whether an overlap exists between the pair of unique nucleic acid reference sequences by comparing the pair of unique nucleic acid reference sequences further cause at least one of the one or more computing devices to:

comparing a circular arrangement of the pair of unique nucleic acid reference sequences when either of a pair of sample records corresponding to the pair of unique nucleic acid reference sequences comprise a nucleic acid type variable set to circular; or comparing a linear arrangement of the pair of unique nucleic acid reference sequences when the pair of sample records corresponding to the pair of unique nucleic acid reference sequences both comprise a nucleic acid type variable set to linear.

20. The at least one non-transitory computer-readable medium of claim 17, wherein the instructions that, when executed by at least one of the one or more computing devices, cause at least one of the one or more computing devices to determine an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints further cause at least one of the one or more computing devices to:

generate an overlap restriction matrix based at least in part on the plurality of nucleic acid overlaps and the maximum overlap constraint, each cell of the overlap restriction matrix corresponding to a pair of unique nucleic acid reference sequences and indicating whether the overlap length between the pair of unique nucleic acid reference sequences exceeds the maximum overlap constraint;

generate a solution matrix comprising a plurality of first groups of cells corresponding to a quantity of unique nucleic acid reference sequences and a plurality of second groups of cells corresponding to a maximum possible quantity of sample pools, wherein each first group of cells corresponds to a unique nucleic acid reference and wherein each second group of cells corresponds to a potential sample pool; and resolve the solution matrix based at least in part on the overlap restriction matrix and an objective function that has a primary objective of minimizing a total quantity of sample pools.

21. The at least one non-transitory computer-readable medium of claim 20, wherein the plurality of first groups correspond to a plurality of columns of cells in the solution matrix and the plurality of second groups correspond to a plurality of rows of cells.

22. The at least one non-transitory computer-readable medium of claim 20, wherein the instructions that, when executed by at least one of the one or more computing devices, cause at least one of the one or more computing devices to determine an optimal grouping of the plurality of samples into a plurality of sample pools based at least in part on the nucleic acid reference sequence of each sample record, the plurality of nucleic acid overlaps between the plurality of unique nucleic acid reference sequences, and one or more constraints further cause at least one of the one or more computing devices to:

balance a quantity of samples in each sample pool in the resolved solution matrix.

23. The at least one non-transitory computer-readable medium of claim 20, wherein the one or more constraints comprise a maximum pool size constraint and wherein the solution matrix is resolved based at least in part on the maximum pool size constraint.

24. The at least one non-transitory computer-readable medium of claim 17, further storing computer-readable instructions that, when executed by at least one of the one or more computing devices, cause at least one of the one or more computing devices to:

generate an electronic file comprising the plurality of sample pools of the optimal grouping, each sample pool identifying one or more samples in the sample pool.

\* \* \* \* \*